United States Patent
Weiβ et al.

(10) Patent No.: US 9,572,913 B2
(45) Date of Patent: *Feb. 21, 2017

(54) USE OF POLYMERIC OR OLIGOMERIC ACTIVE INGREDIENTS FOR MEDICAL ARTICLES

(75) Inventors: André Weiβ, Guxhagen (DE); Thomas Riemann, Groβalmerode (DE); Martin Sippel, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/509,010

(22) PCT Filed: Nov. 12, 2010

(86) PCT No.: PCT/EP2010/067411
§ 371 (c)(1),
(2), (4) Date: Jul. 20, 2012

(87) PCT Pub. No.: WO2011/058148
PCT Pub. Date: May 19, 2011

(65) Prior Publication Data
US 2012/0282213 A1    Nov. 8, 2012

(30) Foreign Application Priority Data
Nov. 12, 2009   (DE) ...................... 10 2009 052 721

(51) Int. Cl.
| | | |
|---|---|---|
| C08G 73/00 | (2006.01) | |
| A61L 29/16 | (2006.01) | |
| A61L 27/14 | (2006.01) | |
| A61L 27/54 | (2006.01) | |
| A61L 29/04 | (2006.01) | |
| A61L 31/04 | (2006.01) | |
| A61L 31/16 | (2006.01) | |
| A01N 47/44 | (2006.01) | |
| C07C 277/00 | (2006.01) | |

(52) U.S. Cl.
CPC ............. *A61L 29/16* (2013.01); *A61L 27/14* (2013.01); *A61L 27/54* (2013.01); *A61L 29/04* (2013.01); *A61L 31/04* (2013.01); *A61L 31/16* (2013.01); *A01N 47/44* (2013.01); *A61L 2300/204* (2013.01); *A61L 2300/404* (2013.01); *C07C 277/00* (2013.01); *Y10T 428/139* (2015.01)

(58) Field of Classification Search
None
See application file for complete search history.

(56) References Cited

U.S. PATENT DOCUMENTS

| | | | |
|---|---|---|---|
| 3,909,200 A | 9/1975 | Redmore | |
| 4,056,508 A | 11/1977 | Schmidt et al. | |
| 5,849,311 A * | 12/1998 | Sawan et al. | 424/406 |
| 6,261,271 B1 | 7/2001 | Solomon et al. | |
| 6,299,892 B1 | 10/2001 | Schmitz | |
| 7,001,606 B2 | 2/2006 | Schmidt et al. | |
| 7,282,538 B2 | 10/2007 | Zheng et al. | |
| 2002/0120333 A1 | 8/2002 | Keogh et al. | |
| 2006/0093573 A1 | 5/2006 | Georgopoulos | |
| 2008/0139450 A1* | 6/2008 | Madhyastha et al. | 514/2 |
| 2009/0130052 A1* | 5/2009 | Schmidt | 424/78.37 |
| 2010/0303752 A1 | 12/2010 | Hametner et al. | |
| 2011/0003689 A1 | 1/2011 | Rosslenbroich et al. | |
| 2012/0259064 A1* | 10/2012 | Greiner et al. | 524/591 |
| 2012/0283664 A1* | 11/2012 | Riemann et al. | 604/264 |

FOREIGN PATENT DOCUMENTS

| | | | | |
|---|---|---|---|---|
| CA | 2 716 805 A1 | 9/2009 | | |
| DE | 19619327 A1 | 11/1997 | | |
| DE | 10355189 A1 | 6/2005 | | |
| DE | 102004011293 A1 | 9/2005 | | |
| EP | 0439698 B1 | 12/1993 | | |
| EP | 1110948 | * 6/2001 | ........... C07C 279/12 | |
| EP | 2305322 A2 | 4/2011 | | |
| GB | 1434040 | * 4/1976 | ............... A01N 9/20 | |
| WO | WO9964550 A1 | 12/1999 | | |
| WO | WO0185676 A1 | 11/2001 | | |
| WO | WO2004052961 | * 6/2004 | ............. C08G 73/00 | |
| WO | WO2005051448 A1 | 6/2005 | | |
| WO | WO2008080184 A2 | 7/2008 | | |
| WO | WO2009009814 A2 | 1/2009 | | |
| WO | WO2009009814 A3 | 1/2009 | | |
| WO | WO2009027186 | * 5/2009 | ............. C08G 83/00 | |
| WO | WO2009080239 | * 7/2009 | ............. A61L 31/16 | |
| WO | WO2009080239 A2 | 7/2009 | | |
| WO | WO2009080239 A3 | 7/2009 | | |

OTHER PUBLICATIONS

Zhang et al. Synthesis and antimicrobial activty of polymeric guanidine and bigunidine salts, Polymer, 1999, vol. 40, p. 6189-6198.*
Xiao et al. Synergy of wet stegth and antimicrobial activity of cellulse paper induced by a novel polymer complex, Material lett. 2008, vol. 62, pp. 3610-3612.*
Oule et al., Polyhexamethylene guanidine hydrochloride-based disinfectant: novel tool to fight meticilin resistant *Staphylococcus aureus* and nosocomial infections, J. Med. Microbio., 2008, vol. 57, pp. 1523-1528.*
Agarwal et al., Phantom Ring-closing condensation polymerization: towards antibacterial oligoguanidines, Macromolecular Rapid Commun., 2011, vol. 32, pp. 994-999.*
Mandolini et al., Ring-closure reactions. 22. Kinetics of Cyclization of diethyl (omega-bromoalkyl)malonates in the ranges of 4- to 21-membered rings. Role of Ring strain J. Am. Chem. Soc., 1984, vol. 106, Abstract.*

(Continued)

*Primary Examiner* — Kevin S Orwig
*Assistant Examiner* — Ping Cao
(74) *Attorney, Agent, or Firm* — Dority & Manning, P.A.

(57) ABSTRACT

The invention relates to the use of polymeric or oligomeric active ingredients having a biocidal effect as additives in the composition of medical articles. The invention further relates to medical articles that comprise such additives.

10 Claims, No Drawings

(56) References Cited

OTHER PUBLICATIONS

Honig et al. (Structure-Activity Relationship of Oligoguanidines-Influence of Counterion, Diamine, Average Molecular Weight on Biocidal Activities, Biomacromolecules, 2003, vol. 4, pp. 1811-1817).*
Tew et al. (Perspective towards self-sterilizing medical devices: controlling infection, Polymer Int., 2008, vol. 57, pp. 6-10).*
Russell, Biocide use and antibiotic resistance, the relevance of laboratory findings to clinical and environmental situations, The Lancet, Infectious Diseases, 2003, vol. 3, pp. 794.*
Search Report for PCT/EP2010/067411 dated Apr. 29, 2011, 3 pages.
Abstract of Austrian Patent No. AT 505514, Feb. 15, 2009.
Abstract of German Patent No. DE 103 55 189 A1, Jun. 30, 2005.
Abstract of German Patent No. DE 196 19 327 A1, Nov. 20, 1997.
Abstract of Chinese Patent—CN101250263, Aug. 27, 2008, 1 page.
Abstract of Russian Patent—RU2144929 dated Jan. 27, 2000, 1 page.

* cited by examiner

USE OF POLYMERIC OR OLIGOMERIC ACTIVE INGREDIENTS FOR MEDICAL ARTICLES

CROSS REFERENCE TO RELATED APPLICATION

This application is the national stage entry of International Patent Application No. PCT/EP2010/067411 having a filing date of Nov. 12, 2010, which claims priority to and the benefit of German Patent Application No. 102009052721.4 filed in the German Intellectual Property Office on Nov. 12, 2009, the entire contents of which are incorporated herein by reference.

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are 1) B. Braun Melsungen AG and 2) Philipps-Universitat Marburg.

The invention relates to the use of polymeric or oligomeric active ingredients having biocidal activity as an additive in a composition for medical articles.

In addition, the invention relates to a process for preparing a medical article, and to a medical article.

Medical articles or objects that are inserted into a patient's body, for example, intravasal catheters, breathing tubes or stents, must have as smooth a surface as possible in order to minimize complaints of the patient and deposits on the surfaces. Such medical articles and their packaging are often prepared by methods of plastics technology, for example, compression molding, extrusion molding, deep drawing and extrusion methods, from a plastic material, wherein it is tried to achieve as smooth surfaces as possible.

In order to avoid infections, it is advantageous for the medical articles to be treated with antimicrobially active agents. High demands are placed on the biocidal treatment of the medical articles, because the articles will contact body tissues and body fluids. For example, catheters, which are inserted through the skin surface into arteries and veins, but also wound or thoracic drainage tubes, are frequent sources of infection. In particular, in patients requiring indwelling urinary catheters, there is a risk of urinary tract infections, which can lead to bacterial or chronic pyelonephritis.

In the medical field, the central venous catheters, in particular, play an increasing role in medical treatments and surgical operations. Central venous catheters are employed more and more often within the scope of intensive care medicine, but also in applications, for example, in bone marrow and organ transplantations, hemodialysis or cardiothoracic surgery.

A similar infection risk exists in all devices that connect the catheters with, for example, infusion containers outside the body, for example, connecting pieces, T pieces, couplings, filters, conduit systems, valves, syringes and multiway stopcocks. For the purposes of this description and the claims, all these objects are referred to as "medical articles".

However, for the medical articles, especially the catheters, not only the high demands placed on a smooth surface, for example, for avoiding or reducing platelet aggregation and biofilm formation, and on the biocidal treatment, which are supposed to prevent the growth of microbes on the surface or even kill the microbes altogether, must be ensured, but it must also be ensured that the biocidal treatment of the medical objects does not adversely affect the material properties of the medical articles. In addition, it must be ensured that the medical articles, especially if contacted with fluid, exhibit a high biocidal effectiveness on the one hand, but are not released into the fluid on the other, in order to avoid enrichment of the biocidally active substances in the body. The release of a biocidally active substance from a medical article upon fluid contact is also referred to as "leaching".

From EP 0 229 862, medical articles made of polyurethane on the surface of which an antimicrobial agent is applied are known. From EP 0 379 269, medical articles, especially tubing, formed from a thermoplastic polymer are known that contain chlorhexidine as an antimicrobially active agent. These articles are prepared by first providing a mixture of chlorhexidine and plastic pellets of a thermoplastic polymer, which is processed into a melt in which the chlorhexidine is uniformly distributed, the melt being extruded through a die to form the medical article. However, the use of biguanide-based biocidal agents, such as chlorhexidine or polyhexamethylene biguanide, is not always satisfactory. In particular, there is a need for improvement in view of the smoothness of the surface of the medical articles and in view of the reduction or control of the leaching effect.

WO 2009/009814 A2 discloses a polymeric dental material comprising a silicate filler modified with a polymeric guanidine derivative based on an alkylene diamine and/or oxyalkylene diamine. The polymeric guanidine derivative poly[2-(2-ethoxyethoxyethyl)guanidinium hydrochloride] is explicitly disclosed, but did not yield satisfactory results in terms of antimicrobial effectiveness and in terms of biocompatibility for applications of class 3 medical products having direct contact with the blood circulation.

In addition, it is the object of the present invention to provide medical articles that have been treated with novel biocidally active substances and are highly effective even in view of the development of resistances of the bacterial strains towards conventional antimicrobial agents.

High demands are placed on biocidally active substances intended for the preparation of medical articles. On the one hand, the biocidally active substances must sufficiently soften under the conditions of the processing technology, namely thermoplastic shaping, such as extrusion or injection molding, and at the temperatures and pressures prevailing therein, must not decompose, and in addition must be compatible with the remaining plastic components of the medical article.

Especially for medical articles being in direct contact with the blood circulation, high demands are additionally placed on biocompatibility, wherein factors such as cytotoxicity, hemolysis or allergic reactions are important. In addition, it is to be avoided that the biocidally active substances are released into the blood while the medical article is provided with a high antimicrobial effectiveness.

The object of the present invention is achieved by the use of novel polymeric or oligomeric active ingredients as additives to materials for medical articles.

Therefore, the present invention relates to the use of a polymeric or oligomeric active ingredient having biocidal activity that is obtainable by the polycondensation of a guanidine acid addition salt with a mixture of amines containing at least one diamine and/or triamine, wherein at least one amine is selected from the group consisting of
i) a diamine having at least one cycloaliphatic residue; and
ii) dialkylene triamine
as an additive in a composition for medical articles.

It has been found that when the mentioned polymeric or oligomeric active ingredients are used in composition containing plastic materials, especially thermoplastic polymers, wherein said plastic materials are employed for preparing medical articles, a very high smoothness of the surfaces of the plastic material can be ensured, which may even exceed that of the plastic material without the added polymeric or oligomeric active ingredients. In addition to the excellent biocidal activity that the polymeric or oligomeric active ingredients provide the compositions for the medical articles with, it has also been surprisingly found that the polymeric or oligomeric active ingredients provide the compositions with a readily controllable release property (leaching effect). The controllability ranges from no release to release rates as high as several mg/m²/h.

In addition, it has been surprisingly found that the polymeric or oligomeric active ingredients to be employed according to the invention have a good biocompatibility, exhibit a high antimicrobial effectiveness against a wide variety of germs, and in addition exert only a slight influence on the thermoplastic polymers required for preparing the medical articles in terms of strength, gloss and durability.

The polymeric or oligomeric active ingredients used according to the invention can be in the form of both homopolymers and copolymers. It is advantageous if the guanidine acid addition salt is guanidinium chloride (or guanidine hydrochloride). However, other guanidine acid addition salts based on inorganic or organic acids are also suitable, for example, the hydroxides, hydrogensulfates and acetates.

The polymeric or oligomeric active ingredients used according to the invention are preferably in the form of their hydroxide salts. These can be obtained, for example, by basic anion-exchange from the corresponding halides, for example, chlorides.

The polymeric or oligomeric active ingredients having biocidal activity are obtainable by the polycondensation of a guanidine acid addition salt with a mixture of amines containing at least one diamine and/or triamine, wherein at least one amine is selected from the group consisting of
i) a diamine having at least one cycloaliphatic residue; and
ii) dialkylene triamine.

The polymeric or oligomeric active ingredients obtainable by the polycondensation preferably have a polyguanidine structure or, especially if dialkylene triamines, for example, diethylene triamine, are used, a polyiminoimidazole structure.

In a preferred embodiment of the present invention, the mixture of amines comprises component i) (diamine having at least one cycloaliphatic residue) and/or component ii) (dialkylene triamine) in an amount of at least 10 mol-%, preferably at least 25 mol-%, more preferably at least 45 mol-%, particularly at least 85 mol-%, especially at least 95 mol-%, respectively based on the total mixture of amines.

Preferably, the mixture of amines includes an alkylene diamine, more preferably a compound of general formula $NH_2(CH_2)_nNH_2$ in which n represents an integer of from 2 to 10, preferably 4 or 6. Preferably employed alkylene diamines have terminal amino groups. Hexamethylene diamine (hexane 1,6-diamine) is particularly preferred. The alkylene diamine can be employed in admixture with other diamines or triamines in the polycondensation reaction, wherein at least one amine is selected from the group consisting of
i) a diamine having at least one cycloaliphatic residue; and
ii) dialkylene triamine,
preferably selected from the group consisting of 4,4'-methylenebis(cyclohexylamine) and/or diethylene triamine to form copolymers.

Preferably, the mixture of amines may further include oxyalkylene diamines.

Suitable oxyalkylene diamines include, in particular, those oxyalkylene diamines that have terminal amino groups, in particular. A preferred oxyalkylene diamine is a compound of general formula $NH_2[(CH_2)_2O]_n(CH_2)_2NH_2$ in which n represents an integer from 2 to 6, preferably from 2 to 5, more preferably from 2 to 4, especially 2. Polyoxyethylene diamines, especially triethylene glycol diamine, are preferred. Polyoxypropylene diamines, especially di- or tripropylene glycol diamine, can be more preferably employed.

In a preferred embodiment, the polymeric or oligomeric active ingredient is in the form of a homopolymer. In such cases, the mixture of amines consists of a diamine having at least one cycloaliphatic residue, or of a dialkylene triamine.

In a further preferred embodiment, the mixture of amines consists of the triamine diethylene triamine. In this variant, the polymeric or oligomeric active ingredient is thus in the form of a homopolymer, for example, poly(iminoimidazole).

In another preferred embodiment, the mixture of amines consists of the diamine 4,4'-methylenebis(cyclohexylamine). Polycondensation with a guanidine acid addition salt yields the homopolymer poly(4,4'-methylenebis(cyclohexylamine hydrochloride), for example.

More preferably, said polymeric or oligomeric active ingredients are obtainable by the polycondensation of a guanidine acid addition salt with a mixture of amines containing at least one diamine having at least one cycloaliphatic residue. Diamines having at least one cycloaliphatic residue include, for example, cycloaliphatic diamines, for example, cyclohexanediamine, cyclopentanediamine and derivatives thereof. Those diamines in which at least one $NH_2$ group is directly bonded to the cycloaliphatic residue are particularly preferred. Those diamines in which both $NH_2$ groups are respectively bonded directly to one and the same cycloaliphatic residue or to different cycloaliphatic residues are particularly preferred. In a particular embodiment, the mixture of amines comprises 4,4'-methylenebis(cyclohexylamine).

In another preferred embodiment of the present invention, the mixture of amines comprises at least one dialkylene triamine. The dialkylene triamines may have alkylene residues of different chain lengths. However, dialkylene triamines in which the alkylene groups have the same length are preferred. Preferred alkylene residues include ethylene, propylene and butylene as well as hexylene. In a particularly preferred embodiment, the mixture of amines comprises the triamine diethylene triamine.

In another preferred embodiment, the polymeric or oligomeric active ingredients used according to the invention are in the form of copolymers. These may be either random or block copolymers. In the case of copolymers, the mixture of amines contains at least two different amines. The mixture of amines contains a first component and at least one second component, wherein
a) the first component is a diamine or triamine selected from the group consisting of
  i) a diamine having at least one cycloaliphatic residue; and
  ii) dialkylene triamine, and wherein
b) the second component is a diamine or triamine selected from the group consisting of
  i) a diamine having at least one cycloaliphatic residue;

ii) dialkylene triamine;
iii) alkylene diamine; and
iv) oxyalkylene diamine; and
wherein the first component is different from the second component.

Those in which the first component is 4,4'-methylenebis(cyclohexylamine) and the second component is selected from diethylene triamine, hexamethylene diamine and triethylene glycol diamine have proven to be particularly suitable copolymeric or cooligomeric active ingredients.

In another preferred embodiment, the copolymeric guanidine derivative contains diethylene triamine as the first component, and the second component is selected from the group consisting of hexamethylene diamine and triethylene glycol diamine.

Especially with respect to the biocidal activity and the leaching behavior in the incorporation of the polymeric or oligomeric active ingredients into plastic materials, especially thermoplastic polymers, which are then processed into medical articles, those copolymeric guanidine derivatives in which at least one component is an alkylene diamine, especially hexamethylene diamine, have proven particularly suitable. Polymeric or oligomeric active ingredients obtainable by the polycondensation of a guanidine acid addition salt with a mixture of amines in which the first component is diethylene triamine and/or 4,4'-methylenebis(cyclohexylamine) and the second component is hexamethylene diamine are particularly preferred.

Mixtures of amines comprising diethylene triamine and hexamethylene diamine are particularly preferred. The active ingredients obtained therefrom not only exhibit excellent antibacterial properties, but are additionally biocompatible, which makes these active ingredients particularly suitable for medical articles being in direct contact with the blood circulation.

In another embodiment, the first component may be diamine having at least one cycloaliphatic residue and/or a dialkylene triamine, and the second component may be an oxyalkylene diamine, especially triethylene glycol diamine.

In the preparation of copolymers, the mixing ratio of the amines to be employed can be widely varied. However, those copolymeric or cooligomeric active ingredients are preferred in which the monomers of the mixture of amines, i.e., the first component and the second component, are in a molar ratio of from 4:1 to 1:4, preferably from 2:1 to 1:2.

The polymeric or oligomeric active ingredients to be employed according to the invention preferably have an average molecular weight (weight average) within a range of from 500 to 7000, especially from 1000 to 5000, daltons.

The polymeric or oligomeric active ingredients used according to the invention all have an antibacterial activity that can be described by means of the so-called "minimum inhibition concentration". This represents the lowest concentration of the bactericide that inhibits the growth of bacteria in a particular solution. A minimum inhibition concentration of less than 50 µg/ml is particularly favorable. Preferably, the polymeric or oligomeric active ingredients to be used according to the invention have a minimum inhibition concentration of less than 10 µg/ml, especially less than 5 µg/ml. The lower this concentration, the more effectively can the corresponding polymeric or oligomeric active ingredient be employed as a biocide.

In a preferred embodiment, the polymeric or oligomeric active ingredients to be employed according to the invention have a minimum inhibition concentration of 50 µg/ml or less, preferably 30 µg/ml or less, more preferably 10 µg/ml or less, especially 5 µg/ml or less.

The polymeric or oligomeric active ingredients to be employed according to the invention can be prepared relatively simply. The polycondensation can be effected by mixing one equivalent of an acid addition salt with one equivalent of the mixture of amines, followed by heating, preferably within a range of from 140 to 180° C., and stirring the melt at elevated temperatures, preferably within a range of from 140 to 180° C., until the evolution of gas is complete. The polycondensation is usually effected within a period of several hours, during which the melt is preferably stirred in a temperature range of 140 to 180° C. A preferred reaction time is from 1 to 15 hours, preferably from 5 to 10 hours.

The process slightly varies depending on the desired final product; for example, for preparing the homopolymer based on 4,4'-methylenebis(cyclohexylamine), it is favorable if the reaction temperature is 170° C. In contrast, the homopolymer prepared on the basis of diethylene triamine may be obtained at 150° C. The preparation of the copolymeric active ingredients to be employed according to the invention is in turn preferably effected within a temperature range of about 170° C.

In addition, it has been surprisingly found that cyclic structures, for example, iminoimidazole structures, may be formed within the polymer units, for example, in the condensation of triamines, so that the active ingredients to be employed according to the invention may be not only polymeric or oligomeric guanidine derivatives, but also polymeric or oligomeric iminoimidazole derivatives.

In particular, it is advantageous if the polymeric or oligomeric active ingredient has a structure selected from the group comprising

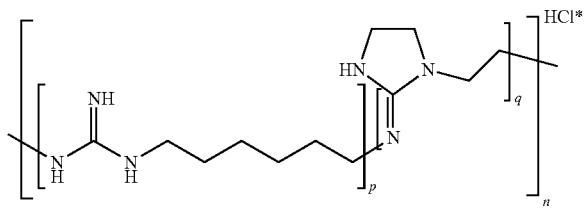

p = 4q

-continued

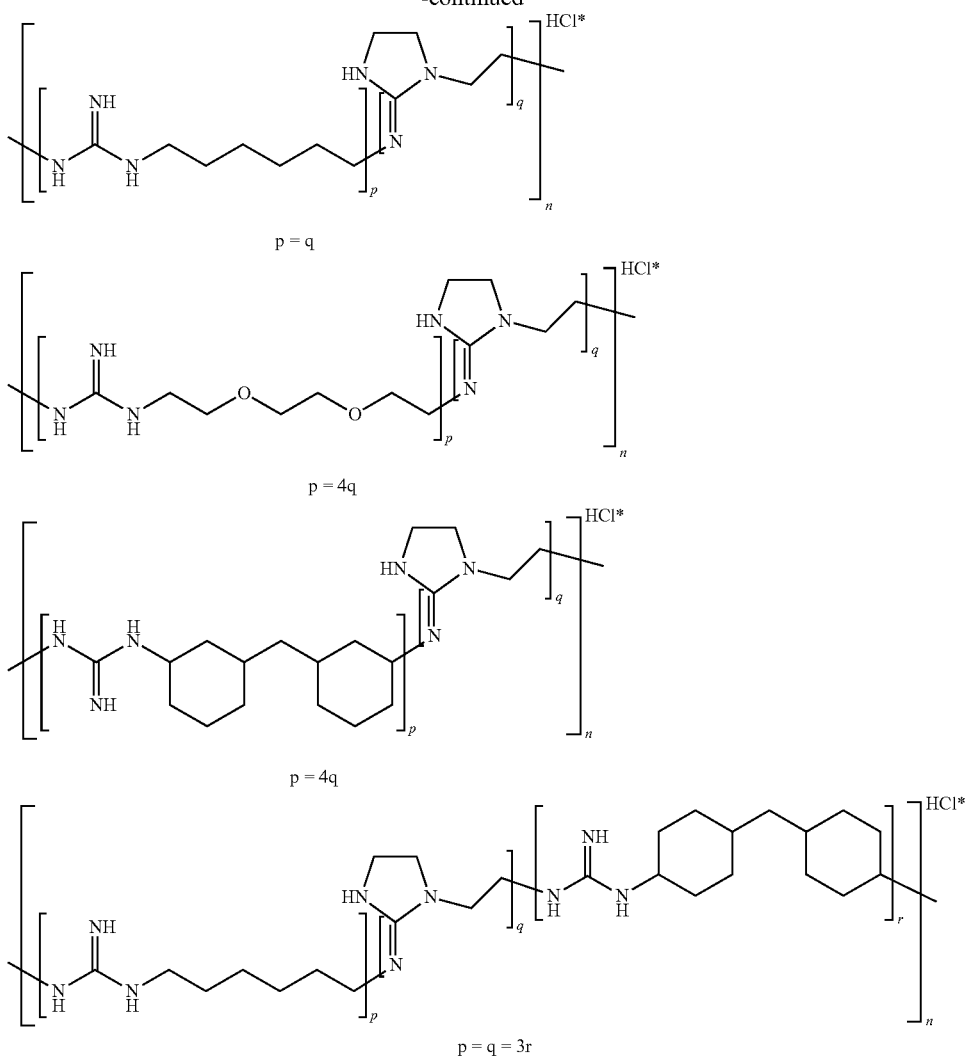

wherein
HCl* means that the HCl is not covalently bonded,
n is a natural number, preferably from 1 to 20, more preferably from 2 to 16, especially from 3 to 8,
p, q and r are integers defining the preferred molar ratio of the structural fragments in the formulas.

In a preferred embodiment of the present invention, the polymeric or oligomeric active ingredients are obtainable by the polycondensation of a guanidine acid addition salt with a mixture of amines containing at least one diamine and/or triamine, wherein at least one amine is selected from the group consisting of
i) a diamine having at least one cycloaliphatic residue; and
ii) dialkylene triamine,
and wherein the mixture of the guanidine acid addition salt and the mixture of amines is heated to a temperature above 140° C., preferably within a range of from 150 to 170° C., and the reaction mixture is maintained at this temperature for at least one hour, preferably at least 5 hours.

According to the invention, the polymeric or oligomeric active ingredients are employed as additives in compositions for medical articles. Depending on the biocidal effectiveness of the polymeric or oligomeric active ingredients and the type and structure of the medical article, the compositions for the medical article may contain the polymeric or oligomeric active ingredient in an amount of at most 10.0% by weight, especially from 0.01 to 5% by weight, and especially in an amount of from 1.0 to 4.0% by weight, respectively based on the composition for the medical article, in a preferred embodiment.

A particular advantage of the polymeric or oligomeric active ingredients to be employed according to the invention is their capability of being incorporated in plastic materials, especially thermoplastic polymers, which often form the essential component of compositions for medical articles. Surprisingly, it has been found that not only can the polymeric or oligomeric active ingredients be incorporated in plastic materials, especially thermoplastic polymer compositions, without a problem, but in addition, the mechanical properties, such as the tensile strength or bending resistance, are not substantially affected thereby. In addition, it has surprisingly been found that the use of the polymeric or oligomeric active ingredients in compositions comprising plastic materials, especially thermoplastic polymers, for medical articles results in extremely smooth surfaces during the processing, and in addition exhibits a controllable leaching effect. Thus, the biocidal polymeric or oligomeric active ingredients can be processed in such a way that they are not leached out of the polymer blend by liquids such as water or ethanol, which is important, for example, for medical articles such as catheters. On the other hand, a controlled release may also be desirable, for example, in wound dressings. The compositions treated with the polymeric or oligomeric active ingredients, especially compositions comprising thermoplastic polymers for medical articles, have an excellent antimicrobial effectiveness, even though they do not exhibit a leaching effect, as with the catheter applications.

In a preferred embodiment, the composition for medical articles further includes plastic materials, especially thermoplastic polymers, especially those selected from polyurethane, polyolefin, polyvinyl chloride, polycarbonate, polystyrene, polyethersulfone, silicone and polyimide. More preferably, the compositions for medical articles include polyurethane, polyethylene or polypropylene.

In a particularly preferred embodiment, the oligomeric or polymeric active ingredient may also be covalently bonded to the thermoplastic polymer. In one embodiment, at least 50% by weight, preferably at least 75% by weight and especially at least 95% by weight of the oligomeric or polymeric active ingredients are covalently bonded to the thermoplast in the compositions for medical articles.

In addition, the compositions for medical articles may contain further usual additives. These include, in particular, fillers that are inert under physiological conditions. Barium sulfate is particularly suitable. For example, a suitable $BaSO_4$ can be purchased from the company Sachtleben Chemie GmbH under the trade name Blancfix®. The fillers are preferably contained in an amount of from 10 to 35% by weight, based on the total mixture, in the compositions for medical articles. Advantageously, the fillers have an average particle size of from 0.01 µm to 10 µm.

However, in a preferred embodiment of the present invention, the composition is substantially free of silicate fillers, because these could adversely affect the surface smoothness and the leaching effect.

According to the present invention, "substantially free" means that the silicate fillers may be present in an amount below 1% by weight, preferably below 0.5% by weight, more preferably below 0.01% by weight, and especially free from any silicate Fillers, the weight percentages being based on the total weight of the composition for the preparation of the medical article.

In particular, medical articles within the meaning of the present invention are selected from the group consisting of central venous catheters; peripheral venous catheters; breathing tubes, stents; products for application in regional anesthesia, especially catheters, couplings, filters; products for infusion therapy, especially containers, ports, conduit systems, filters; accessories, such as connectors, spikes, valves, three-way stopcocks, syringes, conduits, injection ports; products of formulation, especially transfer sets, mixing sets; urological products, especially catheters, urine measuring and collecting devices; wound drains; wound dressing; surgical suture materials; implantation auxiliaries as well as implants, especially plastic implants, for example, hernia meshes, non-wovens, knitwear/knitted fabrics, ports, port catheters, vascular prostheses; disinfectants; disposable surgical instruments; thoracic drains; probes; catheters; housings of medical devices, especially infusion pumps, dialysis devices and screens; artificial dentures; containers for liquids, especially contact lens containers.

Medical articles according to the present invention also include accessory parts for medical products, such as injection-molded parts and other molded parts. The use of the polymeric or oligomeric active ingredients as additives in coatings for surgical suture material is of particular importance.

A preferred medical article according to the present invention is a wound dressing.

Particularly preferred medical articles include tubular medical articles. Such articles have at least one tubular component.

Tubular medical articles within the meaning of the present invention are those medical articles that can conduct fluids. In particular, the medical articles are selected from the group consisting of catheters, central venous catheters, peripheral venous catheters, breathing tubes, stents, couplings, ports, conduit systems, connectors, spikes, valves, three-way stopcocks, syringes, conduits, injection ports, wound drains, thoracic drains and probes.

Particularly preferred medical articles include catheters, especially those prepared by the extrusion of compositions including polyurethane and/or polyethylene and/or polyimide.

A particularly suitable polyamide is obtainable under the trade name Pebax® (Arkema). It is a polyamide that includes polyether blocks.

Because of their excellent antimicrobial activity, the polymeric or oligomeric active ingredients are also suitable as additives for cleaning agents or disinfectants, especially hand disinfectants.

The present invention further relates to a process for preparing a medical article, preferably a tubular medical article, comprising the following steps:
 a) combining and mixing a polymeric or oligomeric active ingredient having biocidal activity that is obtainable by the polycondensation of a guanidine acid addition salt with a mixture of amines containing at least one diamine and/or triamine, wherein at least one amine is selected from the group consisting of
  i) a diamine having at least one cycloaliphatic residue; and
  ii) dialkylene triamine
 with at least one plastic material, preferably a thermoplastic polymer;
 b) subjecting the mixture obtained under a) to one or more shaping methods to form a medical article, preferably a tubular medical article.

Preferred polymeric or oligomeric active ingredients and preferred plastic materials are those mentioned above.

The mixing in step a) is preferably effected by melt-kneading. The polymeric guanidine derivative may be added as an aqueous solution to the molten plastic material, followed by mixing in an extruder. Preferably, the melt-kneading is performed at temperatures above 100° C., more preferably above 150° C.

Preferably, the polymeric or oligomeric active ingredient is subjected to the shaping method in step b) as pellets or as a master batch. The production of pellets can be effected by processes familiar to those skilled in the art of plastics technology. Preferably, the master batch is in the form of pellets containing the polymeric or oligomeric active ingredient in a concentration higher than the final concentration desired for the medical article. Therefore, when a master batch is employed, it is further diluted to the desired final concentration by further adding plastic material.

The shaping method employed in step b) of the process according to the invention is preferably an extrusion method. The latter can be used to prepare, for example, tubular components of the catheter.

The shaping methods are preferably performed at temperatures above the melting point of the mixture prepared in step a), more preferably in a temperature range above 160° C., even more preferably in a range of 180 to 260° C.

As the result, a material with antimicrobial properties is obtained in which the additive (polymeric or oligomeric active ingredient) is physically admixed, or may optionally be chemically bonded to the respective plastic material.

The present invention further relates to a medical article comprising a polymeric or oligomeric active ingredient having biocidal activity that is obtainable by the polycondensation of a guanidine acid addition salt with a mixture of amines containing at least one diamine and/or triamine, wherein at least one amine is selected from the group consisting of
  i) a diamine having at least one cycloaliphatic residue; and
  ii) dialkylene triamine,
and at least one plastic material, preferably a thermoplastic polymer.

Preferred polymeric or oligomeric active ingredients and preferred plastic materials are those mentioned above.

The thermoplastic polymer to be employed in the medical article according to the invention and in the process according to the invention is preferably a thermoplastic polyurethane. Polyurethanes obtainable from a combination of 4,4'-diphenylmethane diisocyanate (MDI) and a polyester- or polyether-based polyol have proven particularly suitable. Advantageously, the polyol includes a polytetramethylene glycol ether. Other suitable thermoplastic polymers that are preferably used in compositions for the medical articles according to the invention are selected, for example, from polyurethane, polyolefin, polyvinyl chloride, polycarbonate, polystyrene, polyethersulfone, silicone and polyamide. More preferably, the compositions for medical articles include polyurethane or polyethylene or polypropylene or polyamide.

Preferred medical articles are those mentioned above. Particularly preferred medical articles are wound dressings and catheters.

Further features, details and advantages of the invention can be seen from the wording of the claims and from the following description of Examples.

Example 1

Synthesis of poly(4,4'-methylenebis(cyclohexylamine)guanidine hydrochloride) (PMBCG)

In an argon countercurrent, 1 equivalent (8.12 g, 85 mmol) of guanidine hydrochloride is added to a 100 ml three-necked flask that had been baked out three times. Subsequently, 1 equivalent (17.88 g, 85 mmol) of 4,4'-methylenebis(cyclohexylamine) was added in a glove box.

The flask is equipped with an internal thermometer and a reflux condenser with a non-return valve according to Stutz (referred to as Stutz condenser in the following) that had been baked out three times.

The reaction mixture is heated in an oil bath, a slow evolution of gas starting from a temperature of 100° C. When the temperature is increased further, the gas evolution only slowly becomes stronger. After a total of 85 minutes, a temperature of 170° C. is reached.

This temperature is maintained for nine hours until the evolution of gas is complete according to visual inspection.

Under ice cooling and in an oil-pump vacuum, the melt is cooled down to room temperature.

Under the conditions mentioned above, the starting amounts employed yield 24.48 g of a transparent, colorless and brittle solid.

The structure of the polymer obtained can be shown according to formula (I).

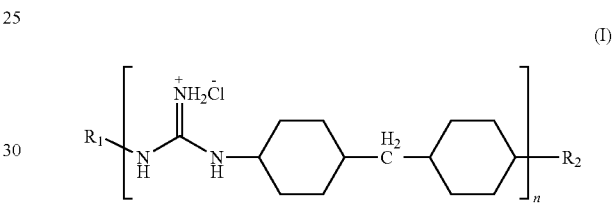

(I)

where n=1 to 8, predominantly 1 to 3.

The residues R1 and R2 may be derived from either the monomer employed or the guanidine hydrochloride employed, and they are therefore defined as follows:

R1 is selected from H or

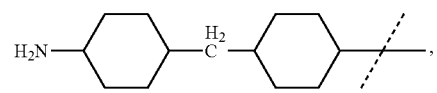

and R2 is selected from $NH_2$ or

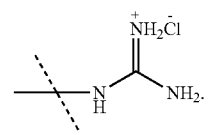

The mixture of products obtained thus contains polymeric compounds corresponding to formulas (II), (III) and (IV):

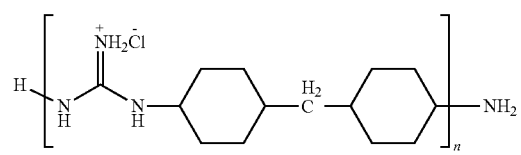

(II)

(III)

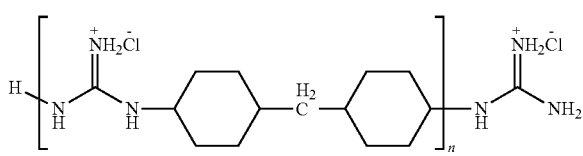

(IV)

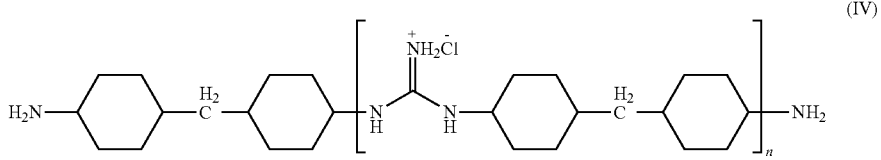

wherein n is defined as in formula (I).

Example 2

Synthesis of a Homopolymer Based on Diethylene Triamine

In a 100 ml three-necked flask with an internal thermometer, Stutz condenser and suction piece with cock that had been baked out three times and filled with argon, 1 equivalent (8.12 g, 85 mmol) of guanidine hydrochloride and 1 equivalent (8.77 g, 85 mmol) of diethylene triamine are heated to a temperature of 150° C. within 50 minutes by means of an oil bath.

From the time when a temperature of 95° C. is reached, an evolution of gas can be observed, which rapidly increases when the temperature is increased further.

The melt is maintained at 150° C. for five hours with stirring until the evolution of gas is complete.

Under ice cooling and in an oil-pump vacuum, the melt is cooled down to room temperature.

Under the conditions mentioned above, the starting amounts employed yield 11.96 g of a white and brittle solid.

Surprisingly, the repeating monomer unit of the polymeric active ingredient obtained shows the cyclic structure according to formula (V):

(V)

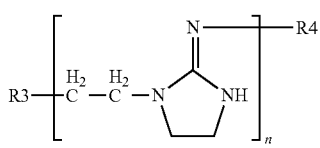

where n=1 to 12, predominantly 2 to 8.
R3 is either NH$_2$ or

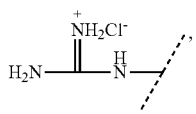

and
R4 is selected from

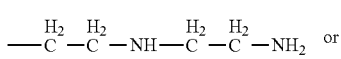 or

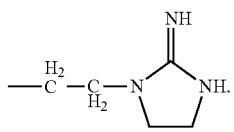

Thus, the product mixture obtained contains polymeric compounds corresponding to formulas (VI), (VII) and (VIII):

(VI)

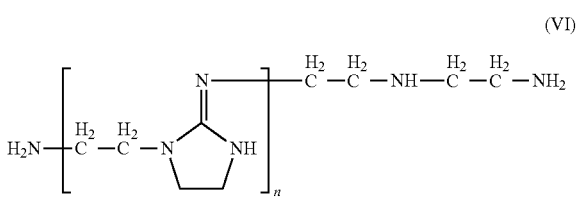

(VII)

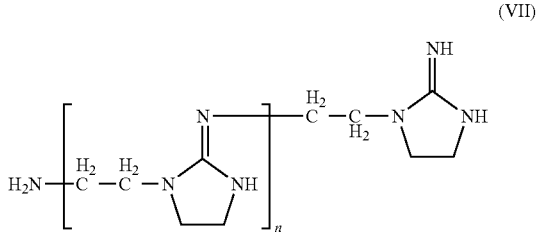

(VIII)

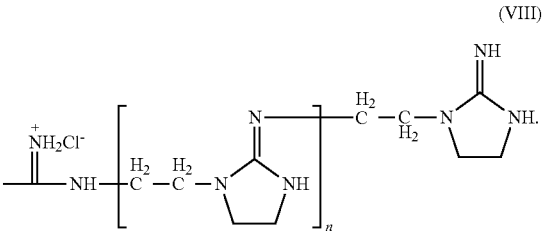

It is conceivable that about 90% of the rings in formulas (VI), (VII) and (VIII) carry a positive charge. It is also conceivable that the positive charge is not localized on one of the nitrogen atoms in the ring, but is rather delocalized. Thus, an alternative form of representing formula (VIII) is the following formula (VIII'):

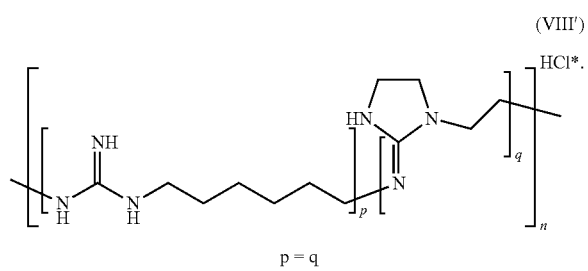

(VIII')

p = q

Formulas (I) to (IV) of Example 2 also can be represented analogously, wherein the positive charge is distributed to all three nitrogen atoms of the guanidine unit in a tautomeric way.

Example 3

Synthesis of Guanidine Copolymers

In a reaction flask prepared in accordance with the above described Examples, 1 equivalent (8.12 g, 85 mmol) of guanidine hydrochloride and 1 equivalent of the comonomers, which are present in a mixing ratio according to Table 1, are commonly heated to a temperature of 170° C. within 30 minutes by means of an oil bath.

The melt is maintained at this temperature for five hours with stirring. Under ice cooling and in an oil-pump vacuum, the melt is cooled down to room temperature.

TABLE 1

Mixing ratios of the di- and triamines employed in the amine mixture for preparing guanidine copolymers

| No. | Monomer 1 | Monomer 2 | Amount of monomer 1 employed | Amount of monomer 2 employed |
|---|---|---|---|---|
| C1 | 4,4'-methylenebis-(cyclohexylamine) | diethylene triamine | 14.30 g<br>68 mmol<br>0.80 eq | 2.21 g<br>17 mmol<br>0.2 eq |
| C2 | 4,4'-methylenebis-(cyclohexylamine) | diethylene triamine | 13.41 g<br>63.75 mmol<br>0.75 eq | 2.77 g<br>21.25 mmol<br>0.25 eq |
| C3 | 4,4'-methylenebis-(cyclohexylamine) | diethylene triamine | 11.92 g<br>56.67 mmol<br>0.67 eq | 3.69 g<br>28.33 mmol<br>0.33 eq |
| C4 | 4,4'-methylenebis-(cyclohexylamine) | diethylene triamine | 8.94 g<br>42.50 mmol<br>0.50 eq | 5.53 g<br>42.50 mmol<br>0.50 eq |
| C5 | 4,4'-methylenebis-(cyclohexylamine) | hexamethylene diamine | 3.58 g<br>17.00 mmol<br>0.20 eq | 7.90 g<br>68.00 mmol<br>0.80 eq |
| C6 | 4,4'-methylenebis-(cyclohexylamine) | hexamethylene diamine | 4.47 g<br>21.25 mmol<br>0.25 eq | 7.41 g<br>63.75 mmol<br>0.75 eq |
| C7 | 4,4'-methylenebis-(cyclohexylamine) | hexamethylene diamine | 5.96 g<br>28.33 mmol<br>0.33 eq | 6.59 g<br>56.67 mmol<br>0.67 eq |
| C8 | 4,4'-methylenebis-(cyclohexylamine) | hexamethylene diamine | 8.94 g<br>42.50 mmol<br>0.50 eq | 4.94 g<br>42.50 mmol<br>0.50 eq |
| C9 | 4,4'-methylenebis-(cyclohexylamine) | hexamethylene diamine | 11.92 g<br>56.67 mmol<br>0.67 eq | 3.29 g<br>28.33 mmol<br>0.33 eq |
| C10 | 4,4'-methylenebis-(cyclohexylamine) | hexamethylene diamine | 13.41 g<br>63.75 mmol<br>0.75 eq | 2.47 g<br>21.25 mmol<br>0.25 eq |
| C11 | 4,4'-methylenebis-(cyclohexylamine) | hexamethylene diamine | 14.30 g<br>68.00 mmol<br>0.80 eq | 1.98 g<br>17.00 mmol<br>0.20 eq |
| C12 | 4,4'-methylenebis-(cyclohexylamine) | triethylene glycol diamine | 13.41 g<br>63.75 mmol<br>0.75 eq | 3.15 g<br>21.25 mmol<br>0.25 eq |
| C13 | 4,4'-methylenebis-(cyclohexylamine) | triethylene glycol diamine | 11.92 g<br>56.67 mmol<br>0.67 eq | 4.20 g<br>28.33 mmol<br>0.33 eq |
| C14 | 4,4'-methylenebis-(cyclohexylamine) | triethylene glycol diamine | 8.94 g<br>42.50 mmol<br>0.50 eq | 6.30 g<br>42.50 mmol<br>0.50 eq |
| C15 | 4,4'-methylenebis-(cyclohexylamine) | triethylene glycol diamine | 5.96 g<br>28.33 mmol<br>0.33 eq | 8.40 g<br>56.67 mmol<br>0.67 eq |
| C16 | 4,4'-methylenebis-(cyclohexylamine) | triethylene glycol diamine | 4.47 g<br>21.25 mmol<br>0.25 eq | 9.45 g<br>63.75 mmol<br>0.75 eq |
| C17 | diethylene triamine | hexamethylene diamine | 1.75 g<br>17.00 mmol<br>0.20 eq | 7.90 g<br>68.00 mmol<br>0.80 eq |
| C18 | diethylene triamine | hexamethylene diamine | 2.19 g<br>21.25 mmol<br>0.25 eq | 7.41 g<br>63.75 mmol<br>0.75 eq |
| C19 | diethylene triamine | hexamethylene diamine | 3.69 g<br>28.33 mmol<br>0.33 eq | 6.59 g<br>56.67 mmol<br>0.67 eq |
| C20 | diethylene triamine | hexamethylene diamine | 5.53 g<br>42.50 mmol<br>0.50 eq | 4.94 g<br>42.50 mmol<br>0.50 eq |
| C21 | diethylene triamine | triethylene glycol diamine | 8.30 g<br>63.75 mmol<br>0.75 eq | 3.15 g<br>21.35 mmol<br>0.25 eq |
| C22 | diethylene triamine | triethylene glycol diamine | 7.38 g<br>56.67 mmol<br>0.67 eq | 4.20 g<br>28.33 mmol<br>0.33 eq |
| C23 | diethylene triamine | triethylene glycol diamine | 5.53 g<br>42.50 mmol<br>0.50 eq | 6.30 g<br>42.50 mmol<br>0.50 eq |

(eq = equivalent)

Example 4

Determination of the Minimum Inhibition Concentration of the Polymeric Guanidine Derivatives Used According to the Invention For testing the biocidal activity of the polymeric guanidine derivatives used according to the invention, the compounds prepared in accordance with one of the previous Examples are added to a bacterial nutrient medium, preferably tryptic soy broth, and diluted to different concentrations.

These solutions of different concentrations are inoculated with a suspension of *Escherichia coli* and incubated at 37° C. for 24 hours.

The "minimum inhibition concentration" (MIC) is the lowest concentration of the biocide to be tested in the solution that still inhibits the growth of the bacteria. In the corresponding solution, turbidity from the growth of the bacteria cannot be observed.

For the homopolymers prepared in Example 1 and Example 2, corresponding to formula (I) and formula (V), and for the copolymers obtained from the comonomer mixtures C1 to C23 mentioned in Example 3, the minimum inhibition concentrations (MICs) as shown in Table 2 are obtained.

TABLE 2

Determination of the minimum inhibition concentration of polymeric guanidine derivatives used according to the invention (MIC = minimum inhibition concentration).

| Compound | MIC [µg/ml] |
| --- | --- |
| Control polymer | 5 |
| corresponding to formula (I) | 5 |
| corresponding to formula (V) | >250 |
| C1 | 7.5 |
| C2 | 22.5 |
| C3 | 25 |
| C4 | 50 |
| C5 | 1.5 |
| C6 | 4.7 |
| C7 | 4.25 |
| C8 | 2.5 |
| C9 | 3.5 |
| C10 | 2.5 |
| C11 | 9.75 |
| C12 | 5.5 |
| C13 | 8.5 |
| C14 | 10 |
| C15 | 10 |
| C16 | 10 |
| C17 | 3 |
| C18 | 10 |
| C19 | 10 |
| C20 | 40 |
| C21 | >50 |
| C22 | >50 |
| C23 | >50 |

A control polymer whose biocidal activity is known and whose minimum inhibition concentration is usually 5 µg/ml was employed as a control.

It is seen that all the polymeric guanidine derivatives used according to the invention, especially the copolymers used according to the invention, have a biocidal effect. In particular, copolymers having hexamethylene diamine as the second monomer show a minimum inhibition concentration that is even below 5 µg/ml:

TABLE 3

Selected copolymers used according to the invention having a particularly low minimum inhibition concentration (MIC).

| Copolymer | Monomer 1 | Monomer 2 | Mixing ratio | Reaction conditions | MIC |
| --- | --- | --- | --- | --- | --- |
| C5 | MBC | HMD | 1:4 | 5 h, 170° C. | 1.5 |
| C6 | MBC | HMD | 1:3 | 5 h, 170° C. | 4.7 |
| C7 | MBC | HMD | 1:2 | 5 h, 170° C. | 4.25 |
| C8 | MBC | HMD | 1:1 | 5 h, 170° C. | 2.5 |
| C9 | MBC | HMD | 2:1 | 5 h, 170° C. | 3.5 |
| C10 | MBC | HMD | 3:1 | 5 h, 170° C. | 2.5 |
| C17 | DETA | HMD | 1:4 | 5 h, 170° C. | 3 |

(MBC = 4,4'-methylenebis(cyclohexylamine), HMD = hexamethylene diamine, DETA = diethylene triamine).

In the polymeric or oligomeric active ingredients having a biocidal activity, used according to the invention, wherein the active ingredient is a product of a polycondensation of a guanidine acid addition salt with a mixture of amines that contains at least one diamine and/or triamine, it is seen that it is particularly favorable if at least one amine is selected from 4,4'-methylenebis(cyclohexylamine) and diethylene triamine. Conveniently, the guanidine acid addition salt is guanidine hydrochloride.

It is further seen that the polymeric or oligomeric active ingredient can be a homopolymer. In this case, it is favorable if the mixture of amines consists of the triamine diethylene triamine, or if the mixture of amines consists of the diamine 4,4'-methylenebis(cyclohexylamine).

It is also seen that the mixture of amines can contain a first component and at least one second component, wherein the first component is a diamine or triamine selected from the group of 4,4'-methylenebis(cyclohexylamine), diethylene triamine, and wherein the second component is a diamine or triamine selected from the group of 4,4'-methylenebis(cyclohexylamine), diethylene triamine, hexamethylene diamine, triethylene glycol diamine, and wherein the first component is different from the second component.

More preferably, the first component is 4,4'-methylenebis(cyclohexylamine), and the second component is selected from diethylene triamine, hexamethylene diamine, triethylene glycol diamine. It is also favorable if the first component is diethylene triamine, and the second component is selected from hexamethylene diamine and triethylene glycol diamine.

The first component and the second component are preferably in a mixing ratio of 4:1 to 1:4. The mixture of amines and the guanidine salt are preferably employed in approximately equimolar amounts.

In the polymeric or oligomeric active ingredients used according to the invention, wherein the active ingredient is a product of a polycondensation of a guanidine acid addition salt with a mixture of amines that contains at least one diamine and/or triamine, it is seen that it is particularly advantageous if they are prepared by a process comprising the steps of providing about one equivalent of guanidine hydrochloride, adding about one equivalent of a mixture of amines containing one or two of the compounds of the group comprising a diamine having at least one cycloaliphatic residue, and dialkylene triamine, heating at 150 to 170° C., and stirring the melt at 150 to 170° C. until the evolution of gas is complete, but at least for 5 hours.

Example 5

General Protocol for Producing a Polyurethane-Based Catheter Tube from TPU Granules Treated with the Polymeric or Oligomeric Active Ingredient to be Employed According to the Invention An aliphatic thermoplastic polyurethane (based on a polytetramethylene glycol ether) is mixed with 10 to 35% by weight, based on the total mixture, of barium sulfate having an average particle size of 0.01 µm to 10 µm and 0.5 to 10% by weight of a polymeric or oligomeric active ingredient to be used according to the invention, and the mixture was extruded. The extrusion was performed using extruders as usual for catheter production, for example, the extruder Maillefer type ED45-30D.

Example 6

Production of a Catheter Tube

The thermoplastic polyurethane Pellethane® 2363-90A (Lubrizol Advanced Materials; U.S.A.) is mixed with 25% by weight barium sulfate having an average grain size of 0.7 µm and 3% by weight of the active ingredient C20, and the mixture was extruded. The extrusion was performed using the extruder Maillefer type ED4530D at temperatures above 160° C.

Example 7

Comparative Example

A piece of catheter tube according to Example 6 is prepared, but without adding a polyguanidine. The pieces of catheter tube prepared according to Examples 6 and 7 were examined by scanning electron micrographs. By optical microscopy, it could already be detected that the pieces of catheter tube according to the invention had a substantially smoother shape as compared to the pieces of catheter tube according to Comparative Example 7.

In addition, the surface roughness $R_z$ [μm] was measured. A surface roughness $R_z$ of 2.91 μm was detected for Comparative Example 7, and a surface roughness $R_z$ of only 2.32 μm was detected for the inventive piece of catheter tube according to Example 6.

Example 8

Comparative Example

A piece of catheter tube according to Example 6 is prepared, but poly[2-(2-ethoxy)ethoxyethyl)guanidinium chloride] is employed in an amount of 3% by weight instead of the polyguanidine to be employed according to the invention.

The pieces of catheter tube according to Example 6 (according to the invention) and according to Comparative Example 8 were subjected to a proliferation test.

The proliferation test is based on the publication Nature Medicine, vol. 6, No. 8, 1053-1056; 2000. Thus, the pieces of catheter tube to be tested are contaminated with different germs, and then the germ growth is observed in comparison with a sample that has not been antimicrobially treated. The time required by the germ growth to reach a predefined value (0.2 onset OD) as compared to a sample that has not been antimicrobially treated is measured. The longer the time, the higher is the antimicrobial effectiveness of the sample against the individual germs.

Table 4 shows the results of the proliferation test using different germs.

TABLE 4

| Germ | Example 8 [h] | Example 6 [h] |
|---|---|---|
| MRSA | 21.0 | 48.0 |
| Staphylococcus epidermidis | 35.5 | 48.0 |
| Staphylococcus aureus | 26.8 | 48.0 |
| Pseudomonas aeruginosa | 0.1 | 48.0 |
| Enterococcus faecalis | 0.3 | 48.0 |
| Klebsiella pneumoniae | | 48.0 |

From the results in Table 4, it is clear that the pieces of catheter tube treated according to the invention are significantly more efficient against MRSA, *Staphylococcus epidermidis*, *Staphylococcus aureus*, *Pseudomonas aeruginosa* and *Enterococcus faecalis*.

The invention claimed is:

1. A process for preparing a medical article, comprising the following steps:
   a) combining and admixing a polymeric or oligomeric active ingredient having biocidal activity that is obtainable by the polycondensation of a guanidine acid addition salt with a mixture of amines containing at least one diamine and/or triamine, wherein at least one amine is selected from the group consisting of
      i) a diamine having at least one cycloaliphatic residue; and
      ii) dialkylene triamine
   with at least one plastic material to form a composition, wherein the at least one plastic material includes thermoplastic polyurethane, wherein the polymeric or oligomeric active ingredient is present in the composition in an amount ranging from 1% by weight to 4% by weight, wherein the polymeric or oligomeric active ingredient is incorporated into the plastic material, and;
   b) subjecting the composition obtained under a) to one or more shaping methods to form a medical article, wherein the polymeric or oligomeric active ingredient has a structure selected from the group comprising

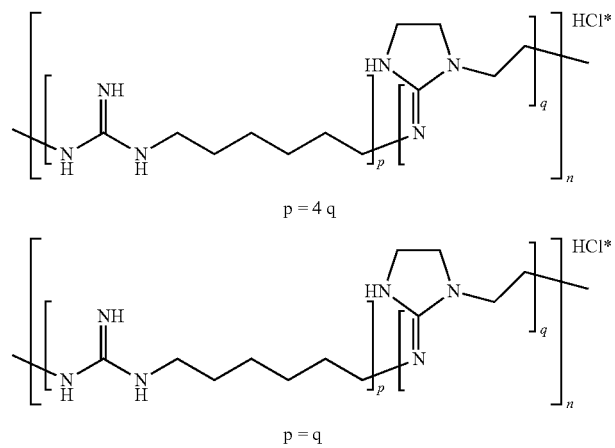

-continued

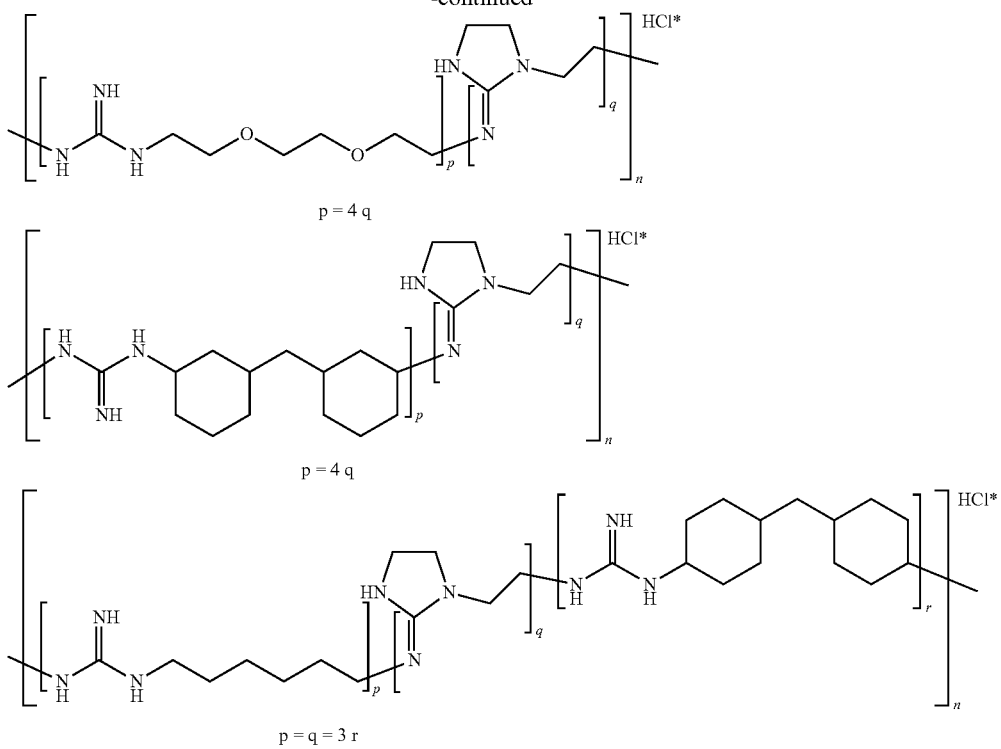

wherein
HCl* means that the HCl is not covalently bonded,
n is a natural number from 1 to 20,
p, q and r are integers defining the preferred molar ratio of the structural fragments in the formulas, wherein the medical article exhibits a surface roughness that is lower than a surface roughness of a medical article comprising a composition that excludes the polymeric or oligomeric active ingredient.

2. The process according to claim 1, characterized in that said polymeric or oligomeric active ingredient is subjected to the shaping method in step b) as pellets or as a master batch.

3. The process according to claim 1, characterized in that said admixing in step a) is performed in an extruder.

4. The process according to claim 1, characterized in that said shaping method is an extrusion.

5. A medical article comprising a composition, wherein the composition comprises, as a first component, a polymeric or oligomeric active ingredient having biocidal activity that is obtained by the polycondensation of a guanidine acid addition salt with a mixture of amines containing at least one diamine and/or triamine, wherein at least one amine is selected from the group consisting of
  i) a diamine having at least one cycloaliphatic residue; and
  ii) dialkylene triamine,
and at least one plastic material, wherein the at least one plastic material includes thermoplastic polyurethane, wherein the polymeric or oligomeric active ingredient and the at least one plastic material are admixed together, wherein the polymeric or oligomeric active ingredient is incorporated into the plastic material, and wherein the medical article exhibits a surface roughness that is lower than a surface roughness of a medical article comprising a composition that excludes the polymeric or oligomeric active ingredient, wherein the polymeric or oligomeric active ingredient has a structure selected from the group comprising

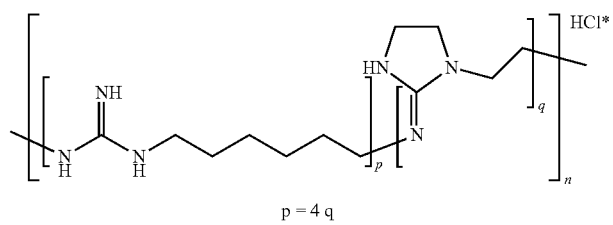

-continued

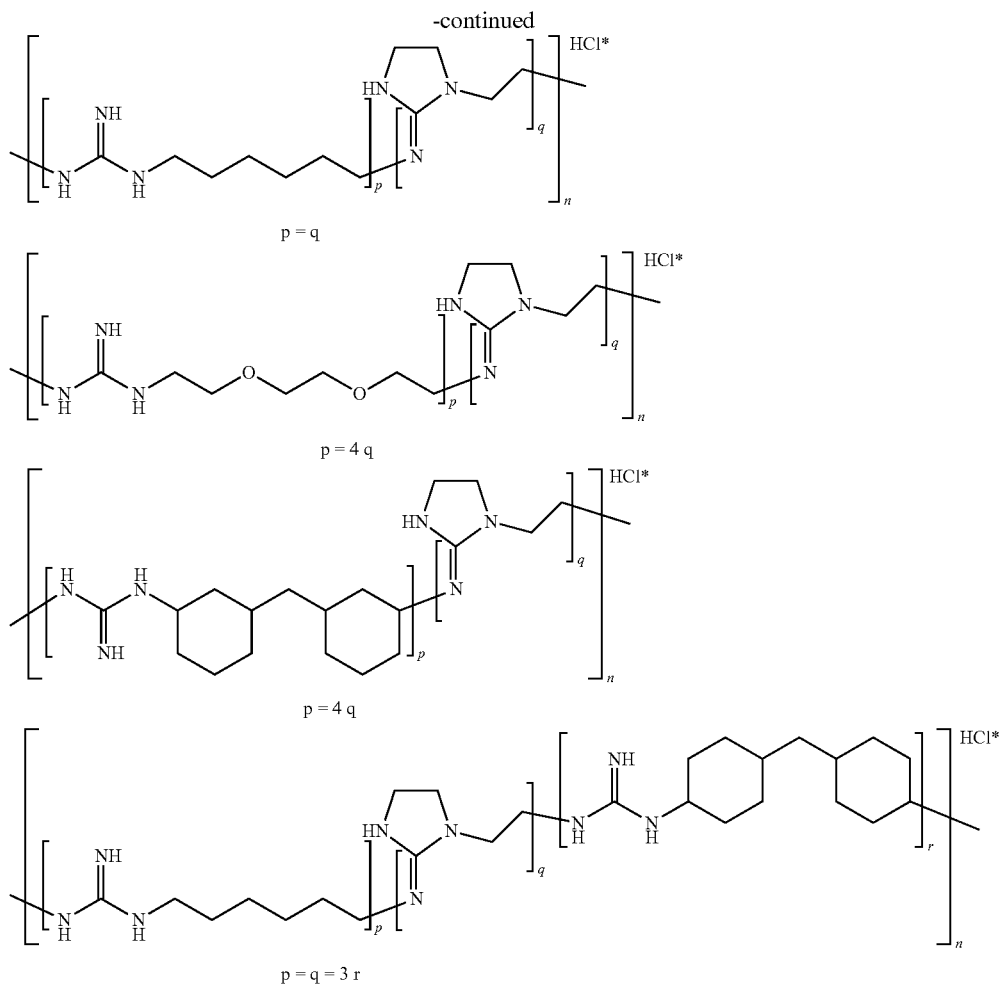

wherein
HCl* means that the HCl is not covalently bonded,
n is a natural number from 1 to 20,
p, q and r are integers defining the preferred molar ratio of the structural fragments in the formulas, wherein the polymeric or oligomeric active ingredient is present in the composition in an amount ranging from 1% by weight to 4% by weight.

6. The medical article according to claim 5, characterized by being a tubular medical article.

7. The medical article according to claim 5, characterized in that said guanidine acid addition salt is guanidine hydrochloride.

8. The medical article according to claim 5, characterized in that said polymeric or oligomeric active ingredient has an average molecular weight within a range of 500 to 7000 Da.

9. The medical article according to claim 5, characterized in that said medical article is selected from the group consisting of central venous catheters; peripheral venous catheters; breathing tubes, stents; products for application in regional anesthesia; products of formulation, mixing sets; urological products, urine measuring and collecting devices; wound drains; wound dressing; surgical suture materials; implantation auxiliaries as well as implants; disposable surgical instruments; thoracic drains; probes; catheters; housings of medical devices; artificial dentures; and containers for liquids.

10. The medical article according to claim 5, characterized in that said medical article is selected from the group consisting of catheters, couplings, filters, containers, ports, conduit systems, connectors, spikes, valves, three-way stopcocks, syringes, conduits, and injection ports.

* * * * *